(12) United States Patent
De Haan et al.

(10) Patent No.: US 9,102,611 B2
(45) Date of Patent: Aug. 11, 2015

(54) EXTRACTION OF CARBOXYLIC ACIDS FROM A DILUTE AQUEOUS STREAM

(71) Applicant: PURAC BIOCHEM B.V., Gorinchem (NL)

(72) Inventors: André Banier De Haan, Best (NL); Agnieszka Krzyzaniak, Norwich (GB); Boelo Schuur, Enschede (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 14/372,079

(22) PCT Filed: Jan. 17, 2013

(86) PCT No.: PCT/NL2013/050022
§ 371 (c)(1),
(2) Date: Jul. 14, 2014

(87) PCT Pub. No.: WO2013/109143
PCT Pub. Date: Jul. 25, 2013

(65) Prior Publication Data
US 2014/0343317 A1    Nov. 20, 2014

(30) Foreign Application Priority Data
Jan. 18, 2012  (EP) .................................. 12151590

(51) Int. Cl.
*C07C 51/48*    (2006.01)
*C07C 51/41*    (2006.01)

(52) U.S. Cl.
CPC ............... *C07C 51/48* (2013.01); *C07C 51/412* (2013.01)

(58) Field of Classification Search
None
See application file for complete search history.

(56) References Cited

FOREIGN PATENT DOCUMENTS

CN    102139970 A    8/2011
WO    WO 93/16173 A1    8/1993

OTHER PUBLICATIONS

Tung et al., "Sorption and Extraction of Lactic and Succinic Acids at pH > $pK_{a1}$.," *Industrial & Engineering Chemistry Research*, vol. 33, No. 12, 1994, pp. 3217-3223.
Wasewar et al., "Fermentation of Glucose to Lactic Acid Coupled with Reactive Extraction: A Review," *Industrial & Engineering Chemistry Research*, vol. 43, No. 19, 2004, pp. 5969-5982.
Krzyzaniak et al., "Extractant Screening for Liquid-Liquid Extraction in Environmentally Benign Production Routes," *Chemical Engineering Transactions*, vol. 24, 2011, pp. 709-714.
International Search Report issued in International Application No. PCT/NL2013/050022 mailed Apr. 24, 2013.
Mar. 19, 2015 Office Action issued in Chinese Patent Application No. 201380005492.7.

*Primary Examiner* — Yevegeny Valenrod
(74) *Attorney, Agent, or Firm* — Oliff PLC

(57) ABSTRACT

A process for removing free carboxylic acid from an aqueous solution including a mass fraction of less than 1% wt of the free carboxylic acid. The process includes the steps of: (a) contacting the aqueous solution with a depleted solvent including a polyamine extractant to obtain an extract enriched in free carboxylic acid and a raffinate having a reduced free carboxylic acid content; and (b) separating the raffinate from the extract, wherein the polyamine extractant is a compound containing at least two nitrogen atoms, and at least one double bond between a nitrogen atom and a carbon atom.

8 Claims, No Drawings

EXTRACTION OF CARBOXYLIC ACIDS FROM A DILUTE AQUEOUS STREAM

FIELD OF THE INVENTION

The present invention provides a process for removing carboxylic acids from a dilute aqueous stream.

There is a growing interest in large-scale production of fermentation chemicals, and in particular in the production of carboxylic acids, such as lactic acid and succinic acid. Such acids can be produced by the fermentation of suitable biomass. In the fermentation of biomass, the pH of the aqueous environment in which fermentation takes place is a critical variable that has to be maintained between predefined levels. The bacteria used in the fermentation process will not survive a concentration of free carboxylic acid that is above 1% wt.

BACKGROUND OF THE INVENTION

In the paper A. Kryzaniak et al, *Extractant screening for liquid-liquid extraction in environmentally benign production routes*, Chemical Engineering Transactions, Volume 24, 2011, p. 709-714 is described an extraction process for removing lactic acid from an aqueous solution. The lactic acid concentration in the examples disclosed in the paper was 0.13 M, which corresponds to 1.2% wt. The extractants used were trioctylamine (TOA), N,N,N',N'-tetramethyl-1,8-naphtalenediamine, N,N-diethyl-m-toluamide, LIX 7950 (LIX 7950 is N,N'-bis(cyclohexyl)-N'''-isotridecylguanidine provided by Cognis) and tetradodecyl-bis-N-oxide. According to the paper, the extractant screening resulted in the conclusion that trioctylamine is the most suitable extractant for removing lactic acid from an aqueous solution, wherein lactic acid is present in a concentration of 1.2% wt.

Bacteria in the biomass used in the fermentation process are adversely affected by a decreasing pH, which is proportional to an increasing concentration of free carboxylic acid in the aqueous solution. Therefore there is a need to remove the carboxylic acid even at low concentrations, below 1% wt and suitably at concentrations below 0.5% wt.

SUMMARY OF THE INVENTION

The present invention provides a process for removing free carboxylic acid from an aqueous solution comprising a mass fraction of less than 1% w of the free carboxylic acid.

To this end the process for removing free carboxylic acid from an aqueous solution comprising a mass fraction of less than 1% w of the free carboxylic acid according to the present invention comprises the steps of:

(a) contacting the aqueous solution with a depleted solvent comprising a polyamine extractant to obtain an extract enriched in free carboxylic acid and a raffinate having a reduced free carboxylic acid content; and (b) separating the raffinate from the extract, wherein the polyamine extractant is a compound containing at least two nitrogen atoms, and at least one double bond between a nitrogen atom and a carbon atom.

Examples of carboxylic acids that can be removed with the process according to the present invention are mono-carboxylic acids, such as acetic acid and propionic acid, hydroxycarboxylic acids, such as 3-hydroxypropionic acid, lactic acid or hydroxybutyric acid and dicarboxylic acids, such as succinic acid, itaconic acid and fumaric acid.

Suitably, the polyamine extractant is a guanidine, $R_5N{:}C(NR_1R_2)(NR_3R_4)$; a dialkylaminopyridine (DAAP); an alkyl-triazabicyclodecene (alkyl-TBD) or mixtures thereof.

In the guanidine, $R_5N{:}C(NR_1R_2)(NR_3R_4)$, the groups $R_1$ through $R_5$ are suitably selected from the group H and an aliphatic group having from 2 to 25 carbon atoms, as described in U.S. Pat. No. 4,992,200, incorporated herein by reference.

DAAP is a dialkylaminopyridine wherein the alkyl groups suitably are aliphatic groups having between 1 and 15 carbon atoms.

Suitably, the alkyl group of the alkyl-triazabicyclodecene comprises an aliphatic group having between 10 and 20 carbon atoms and two secondary alkyl groups of between 5 and 10 at the end of the alkyl group.

The content of free carboxylic acid in the raffinate is such that the raffinate can be returned to the fermenting biomass as a purified aqueous stream.

Surprisingly it was found that trioctylamine (TOA) did not perform as well when removing carboxylic acids from an aqueous stream in which they are present in low concentrations, and that LIX 7950 performed better than could be expected.

For the sake of completeness reference is made to the articles L. A. Tung et al: "Sorption and extraction of lactic and succinic acids at pH>pKa1", Industrial & Engineering Chemistry Research, vol. 33, no. 12, Dec. 1, 1994, pages 3217-3223 and K. L. Wasewar et al: "Fermentation of glucose to lactic acid coupled with reactive extraction: a review", Industrial & Engineering Chemistry Research, vol. 43, no. 19, Sep. 15, 2004, pages 5969-5982. These publications are not relevant to the present invention, because they disclose removing carboxylic acids from aqueous solutions using aliphatic amines of a type differing from the polyamines as used in the process according to the present invention. In addition, International patent application publication No. 93/16 173 relates to decolourizing and deodorizing a fermentation broth using extractants, such as guanidines. This publication is not relevant to the present invention because it relates to decolourizing and deodorizing a fermentation broth at a relatively high pH of 6 to 10, and preferably at a pH of about 7 to 10.

DETAILED DESCRIPTION OF THE INVENTION

The process for removing free carboxylic acid (that is non-dissociated carboxylic acid), such as lactic acid or succinic acid, from an aqueous solution comprising a mass fraction of less than 1% w of the free carboxylic acid, comprises two steps.

In the first step, the aqueous solution is contacted with a depleted solvent comprising the polyamine extractant in an organic solvent to obtain an extract enriched in free carboxylic acid and a raffinate having a reduced free carboxylic acid content.

In the second step the raffinate is separated from the extract. The raffinate has a reduced concentration of free carboxylic acid and can be returned to the fermentation process.

The extract can be further treated to recover the carboxylic acid from it. Examples of the way in which the carboxylic acid can be recovered from the extract have been described in section 12 (Back extraction of lactic acid) of the article K. L. Wasewar et al, *Fermentation of glucose to lactic acid coupled with reactive extraction: a review*, Ind. Eng. Chem. Res., 2004, 53, 5969-5982 (incorporated herein by reference). The extract from which the acid has been removed can be used as a solvent in the first step of the process according to the invention.

The present invention will now be described in more detail with reference to the examples, wherein examples 1 and 2 relate to extracting lactic acid, and example 3 relates to extracting succinic acid.

The extractants used in the examples were: trioctylamine (not according to the invention, obtained from Sigma Aldrich); DAAP12, a dialkylaminopyridine wherein the alkyl groups are aliphatic groups having 12 carbon atoms (synthesized on request); LIX 7950 N,N'-bis(cyclohexyl)-N''-isotridecylguanidine provided by Cognis; and an alkyl-triazabicyclodecene (TBD), wherein the alkyl group comprises an aliphatic group having 15 carbon atoms and two secondary alkyl groups in the form of one hexyl and one octyl group at the end of the alkyl group (synthesized on request).

EXAMPLE 1

Extracting Lactic Acid from an Aqueous Feed with a 10 wt % Extractant Solution

In Example 1 lactic acid was extracted from an aqueous feed of lactic acid (0.12 wt % in water, pH=2.9) at an extraction temperature of 55° C. The extraction process comprised contacting for 17 hours in an incubator 0.005 kg of the aqueous feed with 0.005 kg depleted solvent consisting of 10 wt % extractant dissolved in 1-octanol, to obtain an extract enriched in lactic acid and a raffinate having a reduced lactic acid-content.

Afterwards phases were allowed to settle for 2 hours and a sample of raffinate was taken and the lactic acid concentration was determined with HPLC (Varian Prostar pump, autosampler and UV-detector with Bio-Rad Aminex HPS-87H column and 0.005 M sulphuric acid solution as mobile phase with a flow rate of 0.6 ml/min). The lactic acid concentration in the extract was calculated from a mass balance. To compare different extractants, a distribution coefficient (DLA) of lactic acid was calculated by dividing the concentration of lactic acid (wt %) in the extract by the concentration of lactic acid (wt %) in the raffinate. The results are listed in Table 1.

TABLE 1

Removing lactic acid from an aqueous solution with several extractants.

| Extractant | Distribution coefficient of lactic acid (DLA) |
|---|---|
| Trioctylamine, not according to the invention | 5.3 |
| DAAP12 | 11.7 |
| LIX 7950 | 17.7 |
| TBD | 13.6 |

The results show that at 10 wt % extractant concentration all polyamine extractants yield significantly higher lactic acid distribution coefficients compared to the reference extractant trioctylamine. It can be concluded that the polyamine extractants will yield significantly higher lactic acid extraction efficiencies compared to the reference extractant trioctylamine, which was preferred for removing carboxylic acids from an aqueous stream at higher concentrations.

EXAMPLE 2

Extracting Lactic Acid from an Aqueous Feed with a 20 wt % Extractant Solution at Different Extraction Temperatures In Example 2 lactic acid was extracted from an aqueous feed of lactic acid (0.12 wt % in water, pH=2.9) at extraction temperatures of 25° C. and 55° C. The extraction process comprised contacting for 17 hours in an incubator 0.005 kg of the aqueous feed with 0.005 kg depleted solvent consisting of 20 wt % extractant dissolved in 1-octanol, to obtain an extract enriched in lactic acid and a raffinate having a reduced lactic acid-content.

Afterwards phases were allowed to settle for 2 hours and a sample of raffinate was taken and the lactic acid concentration was determined with HPLC (Varian Prostar pump, autosampler and UV-detector with Bio-Rad Aminex HPS-87H column and 0.005 M sulphuric acid solution as mobile phase with a flow rate of 0.6 ml/min). The lactic acid concentration in the extract was calculated from a mass balance. The distribution coefficient (DLA) of lactic acid was calculated by dividing the concentration of lactic acid (wt %) in the extract by the concentration of lactic acid (wt %) in the raffinate. The results are listed in Table 2.

TABLE 2

Removing lactic acid from an aqueous solution with several extractants at different extraction temperatures.

| | Distribution coefficient of lactic acid (DLA) Extraction temperature | |
|---|---|---|
| Extractant | 25° C. | 50° C. |
| Trioctylamine, not according to the invention | 6.9 | 3.8 |
| DAAP12 | 36 | 16.2 |
| LIX 7950 | 26 | 12.9 |

The results show that 20 wt % extractant concentration the polyamine extractants yield significantly higher lactic acid distribution coefficients compared to the reference extractant trioctylamine at both extraction temperatures. It can be concluded that the polyamine extractants will yield significantly higher lactic acid extraction efficiencies compared to the reference extractant trioctylamine.

EXAMPLE 3

Extracting Succinic Acid from an Aqueous Feed with a 20 wt % Extractant Solution at Different Extraction Temperatures In Example 3 succinic acid was extracted from an aqueous feed of succinic acid (0.15 wt % in water, pH=3.05) at extraction temperatures of 25° C. and 55° C. The extraction process comprised contacting for 17 hours in an incubator 0.005 kg of the aqueous feed with 0.005 kg depleted solvent consisting of 20 wt % extractant dissolved in 1-octanol, to obtain an extract enriched in succinic acid and a raffinate having a reduced succinic acid-content.

Afterwards phases were allowed to settle for 2 hours and a sample of raffinate was taken and the succinic acid concentration determined with HPLC (Varian Prostar pump, autosampler and UV-detector with Bio-Rad Aminex HPS-87H column and 0.005 M sulphuric acid solution as mobile phase with a flow rate of 0.6 ml/min). The succinic acid concentration in the extract was calculated from a mass balance. The distribution coefficient (DSA) of succinic acid was calculated by dividing the concentration of succinic acid (wt %) in the extract over the concentration of succinic acid (wt %) in the raffinate. The results are listed in Table 3.

TABLE 3

Removing succinic acid from an aqueous solution with several extractants at different extraction temperatures.

| Extractant | Distribution coefficient of lactic acid (DSA) Extraction temperature | |
|---|---|---|
| | 25° C. | 50° C. |
| Trioctylamine, not according to the invention | 11.3 | 3.9 |
| DAAP12 | 111 | 24.3 |
| LIX 7950 | 44.7 | 44.1 |

The results show that the polyamine extractants yield significantly higher succinic acid distribution coefficients compared to the reference extractant trioctyl amine at both extraction temperatures. It can be concluded that the polyamine extractants will yield significantly higher succinic acid extraction efficiencies compared to the reference extractant trioctylamine.

The solvent comprising a polyamine extractant suitably further comprises an organic solvent, wherein the organic solvent is suitably octanol, 2-octyl-1-dodecanol, heptane or a mixture thereof.

The invention claimed is:

1. Process for removing free carboxylic acid selected from lactic acid and succinic acid from an aqueous solution comprising a mass fraction of less than 1% wt of the free carboxylic acid, which process comprises the steps of:
   (a) contacting the aqueous solution with a depleted solvent comprising a polyamine extractant in an organic solvent to obtain an extract enriched in free carboxylic acid and a raffinate having a reduced free carboxylic acid content; and
   (b) separating the raffinate from the extract, wherein the polyamine extractant is a compound containing at least two nitrogen atoms, and at least one double bond between a nitrogen atom and a carbon atom.

2. Process according to claim 1, wherein the carboxylic acid is lactic acid.

3. Process according to claim 1, wherein the polyamine extractant comprises a guanidine, R5N:C(NR^R2) (NR3R4), wherein R through R5 are selected from the group H and an aliphatic group having from 2 to 25 carbon atoms.

4. Process according to claim 1, wherein the polyamine extractant comprises a dialkylaminopyridine, wherein the alkyl groups are aliphatic groups having between 1 and 15 carbon atoms.

5. Process according to claim 1, wherein the polyamine extractant comprises an alkyl-triazabicyclodecene, wherein the alkyl group comprises an aliphatic group having between 10 and 20 carbon atoms and two secondary alkyl groups of between 5 and 10 at the end of the alkyl group.

6. Process according to claim 1, wherein the solvent further comprises an organic solvent.

7. Process according to claim 6, wherein the organic solvent is octanol, 2-octyl-1-dodecanol, heptane or mixtures thereof.

8. Process according to claim 1, wherein the carboxylic acid is succinic acid.

* * * * *